Figure 1:
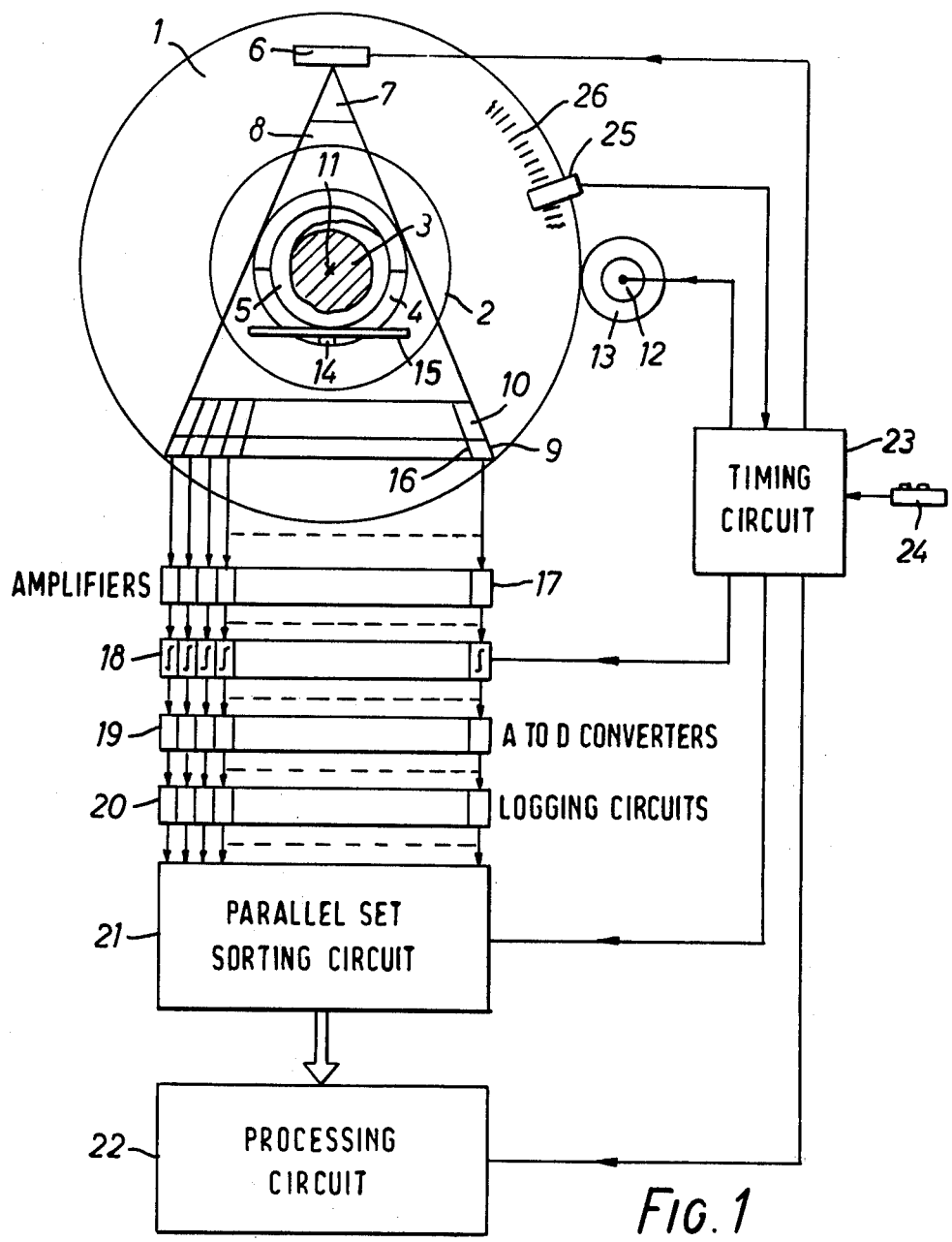

United States Patent [19]

Taylor

[11] 4,048,503

[45] Sept. 13, 1977

[54] RADIOGRAPHY WITH NOBLE GAS CONTAINING DETECTOR CELLS

[75] Inventor: Stanley Taylor, Sunbury-on-Thames, England

[73] Assignee: EMI Limited, Hayes, England

[21] Appl. No.: 693,317

[22] Filed: June 7, 1976

[30] Foreign Application Priority Data

June 10, 1975 United Kingdom ............... 24904/75

[51] Int. Cl.$^2$ ......................... G01T 1/18; G01N 21/34
[52] U.S. Cl. .................................. 250/385; 250/445 T
[58] Field of Search .................. 250/445 T, 385, 363 S

[56] References Cited

U.S. PATENT DOCUMENTS 3,881,110 4/1975 Hounsfield et al. ......... 250/445 T X
3,991,312 11/1976 Whetten et al. ...................... 250/385

Primary Examiner—Davis L. Willis
Attorney, Agent, or Firm—Cooper, Dunham, Clark, Griffin & Moran

[57] ABSTRACT

In a radiographic apparatus, radiation is projected through a substantially planar region of a body along a plurality of beam paths which are laterally and/or angularly displaced from one another. A detecting arrangement is provided for detecting the radiation emergent from the body along each path. The detecting arrangement comprises a plurality of cells containing a noble gas such as xenon. The radiation is periodically interrupted to allow time for each cell to be scavenged of ions produced by radiation traversing one path before radiation is incident on the same cell from another path.

11 Claims, 6 Drawing Figures

RADIOGRAPHY WITH NOBLE GAS CONTAINING DETECTOR CELLS

The present invention relates to radiography, and it relates more particularly to radiographic apparatus for investigating a body by direction radiation through a region thereof along a plurality of substantially co-planar paths and for detecting the amount of radiation emergent from the body along each path. The detected values (or values derived therefrom) are processed to produce a representation fo the absorption (or transmission) coefficient, with respect to the radiation used, of the elements of a matrix of elements notionally delineated in the region. Such apparatus is described, for example, in U.S. Pat. No. 3,778,614.

In some circumstances, such as when the body under examination is the skull of a human patient, the speed at which the examination is carried out is not of critical importance, since, with the use of proper location techniques, the skull can be held in a fixed disposition with respect to the apparatus for a considerable length of time. It is preferable, however, for the examination to be carried out as quickly as possible, at least from the point of view of patient throughput. Moreover, when the torso of a human patient is to be examined, the speed at which the examination is carried out is also of considerable importance from the point of view of the accuracy of the representation, because the torso contains organs which move rhythmically in response to the beating of the patient's heart and/or to his breathing and moreover contains organs which are prone to sudden involuntary movements. Movement during the examination time of organs traversed by the radiation can cause artefacts in, or blurring of, the representation. It is therefore one object of this invention to provide radiographic apparatus of the general nature of that described above but which is capable of examining a body rapidly.

If several of the aforementioned paths are irradiated simultaneously and a suitable number of detectors is provided to allow the radiation emergent along each of the paths to be simultaneously detected, then the examination speed can be increased, as compared with an arrangement in which the paths are irradiated (and/or the emergent radiation is detected) serially. However problems arise in connection with the use of multiple detectors since they tend to drift relative to one another in sensitivity, thereby introducing undesirable artefacts into the representation.

Accordingly it is another object of this invention to provide radiographic apparatus which utilises multiple detectors, and in which several paths can be irradiated simultaneously, in which the detectors are such that the aforementioned problem of relative drift in sensitivity is reduced or eliminated.

According to the invention there is provided radiographic apparatus comprising means defining a patient position, a source of penetrating radiation, such as X-radiation, arranged to project said radiatiion through said position along a plurality of substantially co-planar beam paths, means for scanning said source relative to said patient position so as to project said radiation through said position along further beam paths substantially co-planar with said first-mentioned beam paths, detector means for detecting the radiation emergent from said position along said paths, including a plurality of cells containing a noble gas and means for sequentially deriving, from each cell, output signals indicative of the amount of radiation emergent from said position along a respective group of said paths, said amount being indicated in each case by the number of electrons and ions of said gas generated by radiation projected through the position along the respective path, means being provided for periodically interrupting the incidence of said radiation upon said cells to provide for the clearance from each cell of ions generated by radiation projected through said position along one of said group of paths before the cell is exposed to the radiation projected through said position along the next path of its respective group.

Figure 2:
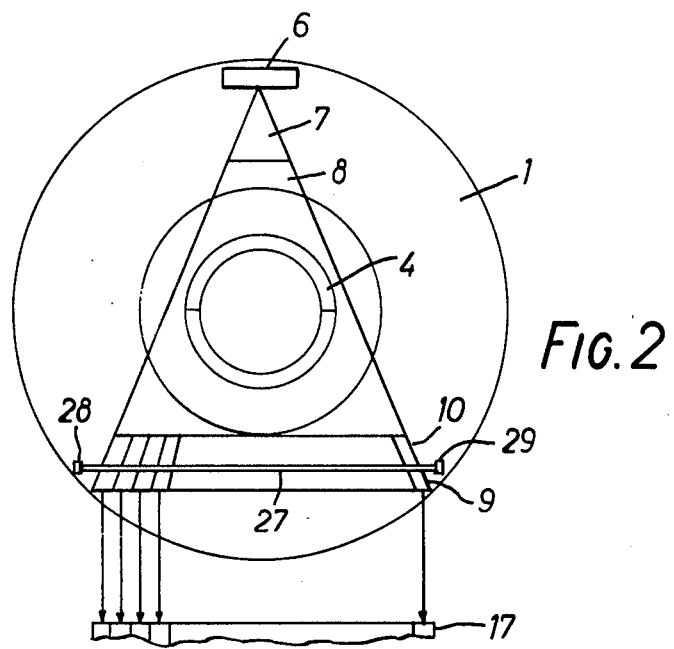
Figure 3:
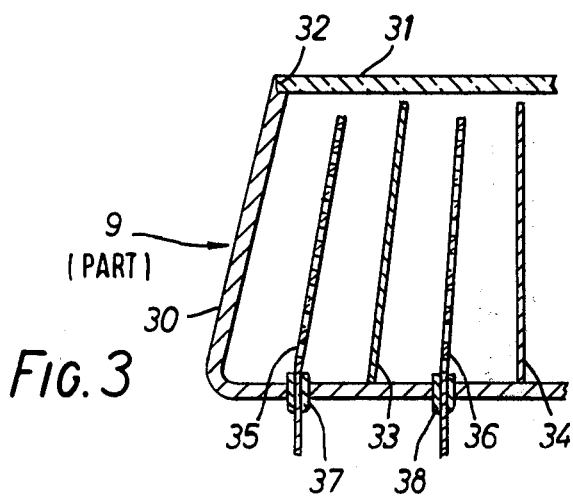
Figure 4:
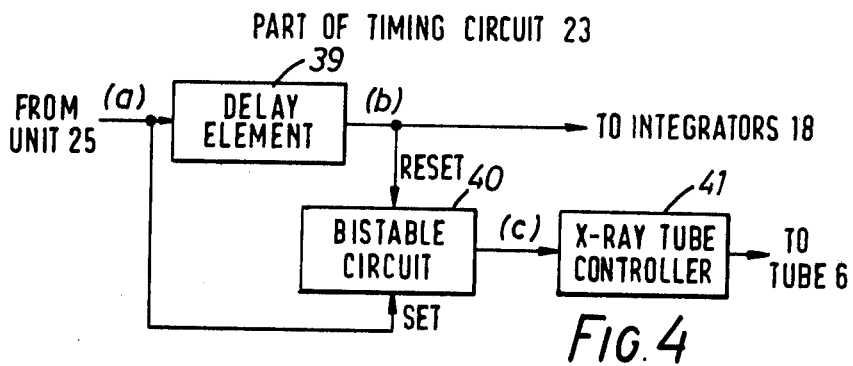
Figure 5:
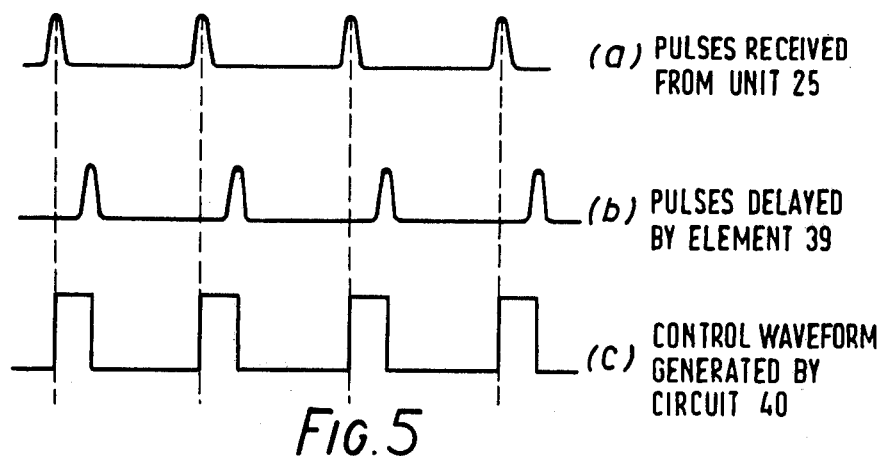
Figure 6:
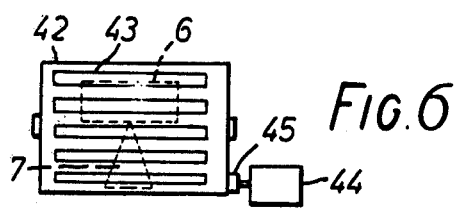

In order that the invention may be clearly understood and readily carried into effect, some embodiments thereof will now be described with reference to the accompanying drawings, of which:

FIG. 1 shows, in schematic plan view, radiographic apparatus in accordance with one example of the invention, including a block diagrammatic representation of some electrical circuits associated therewith, FIG. 2 shows, in similar view to FIG. 1, apparatus in accordance with another example of the invention, FIG. 3 shows, on an enlarged scale, part of a detector arrangement for use with the apparatus shown in either of FIGS. 1 or 2, FIG. 4 shows, in block diagrammatic form, part of a timing circuit referred to with reference to FIG. 1, FIGS. 5(a), (b) and (c) show waveforms explanatory of the operation of the circuit part shown in FIG. 4, and FIG. 6 shows a manner of interrupting X-radiation by means of a drum-like, rotatable shutter member.

Referring now to FIG. 1, a turntable member 1 is formed with a central aperture 2, in which a body 3 to be examined is disposed, within a two-part circular collar 4. Trapped between the collar 4 and the body 3 is a material 5, such as water in a flexible bag, which is provided in order to exclude air from the periphery of the body, at least to such an extent as is practical.

The turntable member 1 carries a rotating anode X-ray tube 6, which constitutes a source of X-rays, and a collimator 7, associated therewith, which selects from the radiation emitted by the tube 6 a sectoral-shaped swath 8 which is substantially planar, the plane of radiation being about 1cm. in thickness. The swath 8 of radiation is disposed as shown in the drawing so that it spans the collar 4. Disposed on the opposite side of the body 3 to the source tube 6, and also carried by the turntable member 1, is a detector arrangement 9, the construction of which will be more fully described hereinafter, and, interposed between the arrangement 9 and the body 3, a bank 10 of collimators.

The turntable member 1 and its attachments are rotatable about an axis 11 in the centre of the aperture 2 by means of a motor 12 which drives a gear wheel 13, the latter engaging with gear teeth (not shown) formed all around the outer periphery of the turntable member 1. The body 3 is held stationary whilst the turntable member 1 rotates around it, and the body is also located so that the swath 8 irradiates a selected substantially planar region of the body. The location of the body 3 in relation to the turntable member 1 and its attachments is achieved by securing a flange 14, formed integrally with the collar 4, to a support member 15 upon which the rest of the body is supported supine. The support member 15 comprises two spaced parts, one in front of the member 1 and one behind it, the gap between the two parts being for the purpose of allowing the radiation to pass through it.

The detector arrangement 9 comprises a tank filled with xenon at a pressure of about five to thirty atmospheres. The tank has dimensions of the order of three to twenty centimeters in depth, to allow a substantial proportion of radiation incident thereon to be absorbed therein, and one centimeter in thickness to accommodate the thickness of the swath 8 of radiation. The breadth of the tank is sufficient to accommodate the breadth of the swath 8. In order to provide a multiple detector arrangement, the tank is divided into a plurality of cells by separators such as 16, suitably formed of tungsten, tantalum, molybdenum, lead-bismuth alloys or platinum (for example) and of thickness about 0.25 mm. Typically there are about 300 cells across the breadth of the tank, each being about one to three millimeters in breadth. Each cell provides output signals, generated by collecting electrons and ions generated by the absorption of the radiation. These output signals are thus indicative of the amount of radiation incident thereon along a path defined by a respective pair of plates in the collimator bank 10; the collimator bank 10 being provided for the purpose of reducing the effects of radiation which, instead of traversing a straight path through the body 3, is scattered by the body. The separators such as 16 are constructed of X-ray absorbent material and reduce cross-talk between cells in the detector arrangement. The thickness mentioned above of either of the materials referred to for this purpose can reduce cross talk by a factor of about $10^4$. Satisfactory results can be obtained, however, with separator thicknesses as low as 0.1mm.

The output signals derived from the cells of detector arrangement 9 are applied to respective amplifiers such as 17 and are thence applied, via respective integrators such as 18, analogue to digital converters such as 19 and logging circuits such as 20 to a circuit 21 which is provided for the purpose of sorting the signals applied thereto into sets which relate to parallel, or substantially parallel, paths through the body. This is done as described, for example, in U.S. Pat. application Ser. No. 544,799, and is done in order that the signals may be applied in suitable form to a processing circuit 22 which preferably performs a convolution of the signals presented thereto, in accordance with the technique described in U.S. Pat. No. 3,924,129 to produce the representation of the aforementioned absorption (or transmission) coefficients.

Since, in general, representations of coefficients are not strictly applicable to the centre points of the elements of the notional matrix referred to previously, the circuit 22 is also preferably arranged to allow for this by effecting an interpolation process which results in the evaluated coefficients being modified appropriately. Such interpolation is described in more detail in U.S. application No. 596,623. Finally, the representation is displayed in any suitable way, for example as a digital computer print-out or on a cathode ray tube.

It will be appreciated that, in order for the detector arrangement 9 to produce output signals relating to a plurality of sets of parallel paths through the body, each set being disposed at a given angle, or mean angle, with respect to the body, the turntable member 1 and its attachments are orbited around the body by means of the motor 12, which latter is controlled by a master timing circuit 23. Circuit 23 also controls the operation of the integrators such as 18, the circuit 21 and the circuit 22 and receives input signals from a manually operable starting switch 24 and from a fixed photocell/detector unit 25 which co-operates with an annular graticule, part of which is shown at 26, formed on turntable member 1 to produce timing signals which are indicative of the progress of the orbital motion of member 1.

Since the integration of the output signals effected by the integrators such as 18 has to be carried out over a finite time and since the member 1 rotates smoothly throughout the examination, it will be appreciated that the output signals from each cell are integrated while the tube 6 and the detector arrangement execute a small but finite angular movement relative to the body. The integration times for all detector cells are the same and they are determined by the circuit 23 in response to the signals supplied thereto from the photocell/detector unit 25. It will be appreciated that there are many integration periods, for example five hundred, during a single revolution of the turntable member 1.

With particular reference to the detector arrangement 9 it has been discovered that, whilst the xenon detector arrangement is substantially free of drift error, it is necessary for the charge, built up in a cell during one integration period in response to the radiation traversing one path through the body, to be removed before radiation is received in the same cell during the next integration period and relating to another path through the body. This is necessary in order to achieve good signal-to-noise performance. Consequently, in this example of the invention, the emission of radiation by the tube 6 is periodically interrupted, once per integration period, in response to signals generated by the timing circuit 23, in order to allow the residue, consisting mainly of positive ions, of the accumulated charge relating to the radiation traversing the first mentioned path to be removed, whilst the radiation is interrupted. Such interruption can be achieved by turning the electron beam of the tube 6 off with appropriate timing by applying a suitable waveform to the operating grid electrode of the tube 6. Alternatively, if the tube 6 is provided with suitable deflection coils, and a suitable waveform is applied thereto from circuit 23, the electron beam of the tube 6, instead of being turned on and off, can be deflected off the rotating anode during the periods when it is desired to interrupt the radiation. As a further alternative, the rotating anode of the tube 6 can be formed such that alternate segments thereof are omitted, rather in the manner of a toothed wheel, and rotating the anode at a rate such that the desired interruptions are provided by the electron beam passing between adjacent "teeth" of the anode. As a still further alternative shown in schematic form in FIG. 6, a hollow, drum-like shutter 42 can be arranged to surround the source tube 6 and the collimator 7, having its axis of symmetry disposed in the plane of the swath 8 and parallel to the axis of the tube 6, the drum having slots formed therein and being rotatable about its axis of symmetry by means of a motor 44 driving a gear wheel 45 which co-operates with teeth (not shown) all around the inner periphery of drum 42, that the swath 8 is alternately transmitted through the apertures of the drum and interrupted by the intervening portions of the drum.

It will be appreciated from the foregoing that the detector arrangement is such as to provide output signals both when the radiation is interrupted and when it is not, though the majority of the output signal from a cell is obtained when the radiation is incident thereon; the output signals derived during periods when the radiation is interrupted relating only to the aforementioned residue of positive ions.

The length of time for which the radiation needs to be interrupted after the irradiation of each path, in order to permit the residue of positive ions to be removed, depends on the parameters of the detector arrangement such as the cell dimensions, the pressure of the xenon and the potentials applied across electrodes used to derive the output signals from the cells. A typical time is about 0.5ms. Thus in a typical case, during the final 0.5ms of each integration period the radiation is prevented from impinging on the cells to allow the positive ions to be scavenged.

One way in which the periodic interruption of the radiation from tube 6 can be effected will now be described with reference to FIG. 4 which shows, in block diagrammatic form, part of the timing circuit shown at 23 in FIG. 1, and FIGS. 5(a) to (c) which show waveforms explanatory of the operation of the circuit components shown in FIG. 4. The timing pulses from the photocell/detector unit 25 are applied in parallel, to a delay element 39 and to the 'SET' input of a bistable circuit 40. The delay element 39 is arranged to impart, to the timing pulses applied thereto, a delay equivalent to the required ion scavenging period, i.e., 0.5ms in this example. The delayed pulses are used as the reading and resetting pulses for the integrators 18 (FIG. 1) and are also applied to the 'RESET' input of the bistable circuit 40. This latter circuit produces a control waveform which is applied to an X-ray tube controlling circuit 41 and used to interrupt the radiation during the interval between the application to circuit 40 of a timing pulse and its delayed counterpart. The control waveform may be used to switch off the electron beam of tube 6 at the appropriate times or to deflect the electron beam away from the target of the tube or to synchronise the rotation of a shutter or the rotating anode of the tube as the case may be.

The waveforms shown in FIGS. 5(a), (b) and (c) represent those occurring at the correspondingly labelled parts of the arrangement shown in FIG. 4.

In the example of the invention illustrated in FIG. 2, wherein components which are common with the apparatus described with reference to FIG. 1 are identified by the same reference numerals, a different technique is used for ensuring that the charges built up in the detector cells during the irradiation periods are removed in producing output signals. In the apparatus shown in FIG. 2, the detector arrangement 9 contains twice as many detector cells as the arrangement 9 described with reference to FIG. 1, and alternate detector cells are considered to constitute one set, whilst the interleaving cells are considered to constitue another set. The arrangement is such that whilst one set of cells is exposed to the radiation, the other set is shielded from the radiation and vice versa. Each shielding period is arranged to be long enough to permit the charge built up during the preceding irradiation period to be removed, and the shielding is effected by means of a shutter member 27 which is interposed between the bank 10 of collimators and the detector arrangement 9 and is arranged to oscillate to and fro in the plane of the swath 8, through a distance equal to the breadth of a cell, at a rate of about 1kHz. This oscillation of the shutter member 27 could be effected mechanically, but it is preferable for the shutter member to be driven under the influence of two piezoelectric transducers 28, 29 one at either end of the member 27. The transducers 28 and 29 are supplied with operating waveforms from the master timing circuit 23, the waveforms being, for example, square or sinusoidal and of the required frequency and displaced in phase by 180° with respect to one another, so that the transducers operate with one pushing the member 27 and the other pulling it, and vice versa.

Other forms of transducer could be used, for example electrostrictive or magnetostrictive transducers, or the member could be formed at either end with a ferromagnetic core, the cores being surrounded by respective solenoid windings which are energised by the master timing circuit 23 with suitable waveforms to produce electro-magnetic deflection of the member 27.

The member 27 is arranged to move in a linear guide (not shown) which locates it accurately in position between the collimator bank 10 and the detector arrangement 9. Moreover, if desired, the oscillatory motion can be monitored by any suitable means, such as a vernier graticule and a photocell/detector device or a laser phase sensitive arrangement, and the monitored information can be supplied to the master timing circuit in order that the latter may modify the waveform supplied to the transducers such as 28 and 29 in the event of the motion departing from the desired motion in either frequency or amplitude.

The processing circuits used in conjunction with the apparatus shown in FIG. 2 are the same as those described with reference to FIG. 1. As has been mentioned, there are twice as many detector cells in the apparatus of FIG. 2 than in the FIG. 1 apparatus. However, it is possible for adjacent cells to share a common amplifier in time multiplex, since one cell is shielded whilst the adjacent cell is being irradiated and, as aforementioned, the majority of the output from a cell is obtained during the irradiation periods. When this expedient of time multiplexing is used, the aforementioned signals indicative of residue are ignored. The time multiplexing can be carried out under the control of a suitable switching waveform derived from the master timing circuit 23.

In both of the arrangement described hereinbefore, i.e., with reference to FIGS. 1 and 2, the amplifiers are provided in integrated circuit form and may if desired, be mounted on the turntable member 1. In any event, the output signals from the components mounted on the turntable 1 can be connected to the processing circuits (which are not carried on the turntable member) by way of slip rings (not shown) or any other suitable technique.

One alternative technique which could advantageously be used for transferring the output signals to the stationary circuit components is to connect each detector cell to a respective sample and hold circuit, the sample and hold circuits being connected to a multiplexer which is arranged, at suitable times during the examination, to scan all of the sample and hold circuits and to transmit their contents by way of a radio link to a demultiplexer which feeds the various amplifiers 17. Of course, if the arrangement of FIG. 2 is used, then each cell requires its own amplifier and two sets of sample and hold circuits and two multiplexers and demultiplexers are required, one for each set.

It is desirable in some circumstances to arrange for the body 3 to be displaced step-wise through the aperture 2 after each of a number of complete revolutions performed by the member 1. This enables the swath 8 to pass through respective planes of the body, which planes are substantially parallel to one another, for different revolutions of the turntable member 1. Such step-wise motion of the patient is preferably achieved by means of an electric motor (not shown) which is operated under the control of master timing circuit 23 to drive the support member 15, together with the collar 4 and the body 3, by the required distance in a direction perpendicular to the plane of the swath. It will be appreciated that such step-wise motion takes a finite time to achieve, and during this time it is preferable to allow the turntable member 1 to continue its rotation. Thus a convenient arrangement is to cause the turntable member to perform a first rotation with the radiation source 6 active and the swath 8 intersecting a first plane of the body, a second rotation with the source inactive whilst the body is moved to a new position, a third rotation with the source active and the swath 8 intersecting a second plane of the body, parallel to the first, a reversal of the direction of rotation whilst the body is moved to another new position and so on. Usually up to eight positions of the body relative to the swath 8 are employed, the direction of rotation being reversed after every three revolutions of member 1. This procedure also has the advantage that the anode of the tube 6 is cooled to some extent during the revolutions and reversals of direction of rotation performed with the tube inactive.

The reversals are necessary to allow conduits supplying coolant or power to the X-ray tube to be wound and unwound on suitable supports to as to avoid the use of considerable lengths of such conduit.

Of course, if the rotational speed of turntable member 1 is high, and the reversals are less frequent or unnecessary, the arrangement could be such that two (or more) rotations of the member 1 are carried out with the source 6 inactive whilst the body is being moved.

FIG. 3 shows, on an enlarged scale, a part of the detector arrangement 9. The arrangement consists of a tank 30 made of a convenient metal, which is preferably electrically conductive. As previously mentioned, the tank 30 contains xenon under a pressure of about five to thirty atmospheres. The radiation enters the tank 30 through a window 31 of low X-ray absorption, which is formed of glass, quartz, aluminium alloy, beryllium or resin bonded carbon fibre composite for example, which window is sealed to the metal tank as shown at 32 by a suitable pressure seal of known kind.

The cell separators referred to hereinbefore are shown at 33 and 34. These separators are secured in physical and electrical contact with the metal of tank 30 so that the separators, apart from reducing cross-talk between cells, also serve as one electrode from each cell. For rigidity, the separators are preferably also secured, by means not shown, to one another and/or to the window 31. The collector electrode in each cell can consist of one or more wires, a thin metal sheet, metallised layers on either side of an insulating sheet, or, as shown, is a grid or mesh electrode, as at 35 and 36, and each such electrode is hermetically sealed through the base of the tank 30 by means of electrically insulating material as shown at 37 and 38. Alternatively, the electrodes such as 35, 36 may be connected to respective pins sealed through the base of the tank 30.

In operation, a suitable potential (e.g. 500V) is applied between the collector electrode 35 or 36 and the metal of the tank 30, which permits electrons and ions, produced in the zenon by the incident radiation, to be collected and applied to the respective amplifier. Each incident photon of radiation produces about $2 \times 10^3$ ions in the xenon, so that a useful amplification effect is achieved.

It is known that xenon cells exhibit an avalanche effect if the applied potential exceeds a certain value, and it can be preferable to operate the detector arrangement so that the cells operate just below the avalanche level.

It will be appreciated that the potential difference between the collector electrode 35 or 36 and the base 30 and separators 30 is continuously applied.

It will also be appreciated by those skilled in the art that, in order to reduce the sensitivity of the collector electrodes to vibration (a phenomenon known as microphony) the collector electrodes should be as rigid as possible. Suitable forms for these electrodes comprise grids, taut wires, meshes in a rigid frame, corrugated structures or egg-box like structures.

As a further modification, applicable to either of the arrangements shown in the drawings, a suitable attenuating means can be placed between the collimator 7 and the body, in the plane of the swath 8, to compensate at least in part for the unequal lengths through the body which are traversed by radiation near the extremes of the swath 8 as opposed to radiation disposed more centrally of the swath. Such attenuating means is arranged to rotate around the body with the member 1.

The scanning arrangement illustrated in FIGS. 1 and 2 is shown by way of example only. The scanning could alternatively comprise, for example, an arrangement such as that described in U.S. Pat. No. 3,946,234 in which a fan-shaped spread of radiation containing at least two divergent beams is scanned laterally across the body, and also rotated around the body at a rate which takes into account the angle of the spread.

Although the invention has been described in relation to embodiments in which xenon is used as a detector, other noble gases such as argon could be used as an alternative.

What I claim is:

1. Radiographic apparatus comprising means defining a patient position, a source of penetrating radiation, such as X-radiation, arranged to project said radiation through said position along a plurality of substantially co-planar beam paths, means for scanning said source relative to said patient position so as to project said radiation through said position along further beam paths, detector means for detecting the radiation emergent from said position along said paths, including a plurality of cells containing a noble gas and means for sequentially deriving, from each cell, output signals indicative of the amount of radiation emergent from said position along a respective group of said paths, said amount being indicated in each case by the number of electrons and ions of said gas generated by radiation projected through the position along the respective path, means being provided for periodically interrupting the incidence of said radiation upon said cells to provide for the clearance from each cell of ions generated by radiation projected through said position along one of said group of paths before the cell is exposed to the radiation projected through said position along the next path of its respective group.

2. Apparatus according to claim 1 wherein said source of radiation comprises an X-ray tube and said means for interrupting comprises control means for periodically interrupting the electron beam of said tube.

3. Apparatus according to claim 1 wherein said means for interrupting comprises mechanically operable shutter means disposed in the path of said radiation.

4. Apparatus according to claim 3 wherein two sets of said cells are provided and said shutter means is adapted to shield one set of cells whilst the other set is irradiated and vice-versa.

5. Apparatus according to claim 1 wherein said noble gas comprises xenon under pressure.

6. Apparatus according to claim 1 wherein said detector means comprise a tank of unitary construction containing said noble gas and separators of X-ray absorbent material defining said cells.

7. Apparatus according to claim 6 wherein said separators are formed of a material selected from the group consisting of tungsten, tantalum, molybdenum, platinum, and lead-bismuth alloy.

8. Apparatus according to claim 7 wherein the thickness of said separators is about 0.25mm.

9. Apparatus according to claim 1 wherein said means for deriving output signals comprises, for each cell, an electrode arrangement comprising a first electrode disposed substantially centrally of said cell and pointing towards said source and at least one further electrode disposed at or adjacent an edge of said cell, means being provided for establishing a potential difference between said first and further electrodes.

10. Apparatus according to claim 9 wherein said cells include separators formed of electrically conductive material and defining said cells and said at least one further electrode is constituted by a separator.

11. Apparatus according to claim 10 wherein said tank is formed of electrically conductive material and said separators are in electrical contact with said tank.

* * * * *